US00PP11095P

United States Patent [19]

Stemkens

[11] Patent Number: Plant 11,095

[45] Date of Patent: Oct. 12, 1999

[54] VERBENA PLANT NAMED 'FLORENA'

[75] Inventor: Henricus G. W. Stemkens, Hoorn, Netherlands

[73] Assignee: Novartis Seeds B.V., Enkhuizen, Netherlands

[21] Appl. No.: 08/994,819

[22] Filed: Dec. 19, 1997

[51] Int. Cl.[6] ..... A01H 5/00

[52] U.S. Cl. ..... Plt./308

[58] Field of Search ..... Plt./87, 308

[56] References Cited

PUBLICATIONS

Peter Walton, Principles and Practices of Plant Science, Prentice Hall. New Jersey, pp. 29–30, 1988.

Hortus Third: A Concise Dictionary of Plants Cultivated in the United States and Canada. Bailey et al. MacMillan Pub. New York, 1976.

UPOV ROM 1998/01, Plant Variety Database, GTI Jouve Retrieval Software, citation for 'Florena', Oct. 1996.

*Primary Examiner*—Howard J. Locker
*Assistant Examiner*—Anne Marie Grünberg
*Attorney, Agent, or Firm*—Thomas Hoxie

[57] ABSTRACT

A new Verbena plant particularly distinguished by its large Neon-rose flower, early flowering, and a semi-erect habit that becomes spreading as plant develops.

2 Drawing Sheets

BACKGROUND OF THE NEW PLANT

The present invention comprises a new distinct cultivar of Verbena, botanically known as *Verbena×hybrida*. The new cultivar is propagated from cuttings resulting from the cross of W720 and T593. W720 is a Rose flowering Verbena having a spreading habit. W720 is not commercially available and is not known by any synonyms. T593 is a Scarlet flowering Verbena having a semierect habit. T593 is not commercially available and is not known by any synonyms. Neither W720 or T593 has been patented. As a result of this cross the present cultivar was created in 1995 in Enkhuizen, Netherlands and has been repeatedly asexually reproduced by cuttings in Enkhuizen, Netherlands and Sarrians, France over a two year period. It has been found to retain its distinctive characteristics through successive propagations, and this novelty appears to be firmly fixed.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on plants that were 18 weeks old, blossomed under natural light in a greenhouse. Color readings were taken in the greenhouse under ambient light. Color references are primarily to The R.H.S. Colour Chart of The Royal Horticultural Society of London.

DESCRIPTION OF THE DRAWING

This new Verbena plant is illustrated by the accompanying photographic drawings which show blooms, buds and foliage of the plant in full color, the color shown being as true as can be reasonably obtained by conventional photographic procedures.

The Plant

Figure 1:
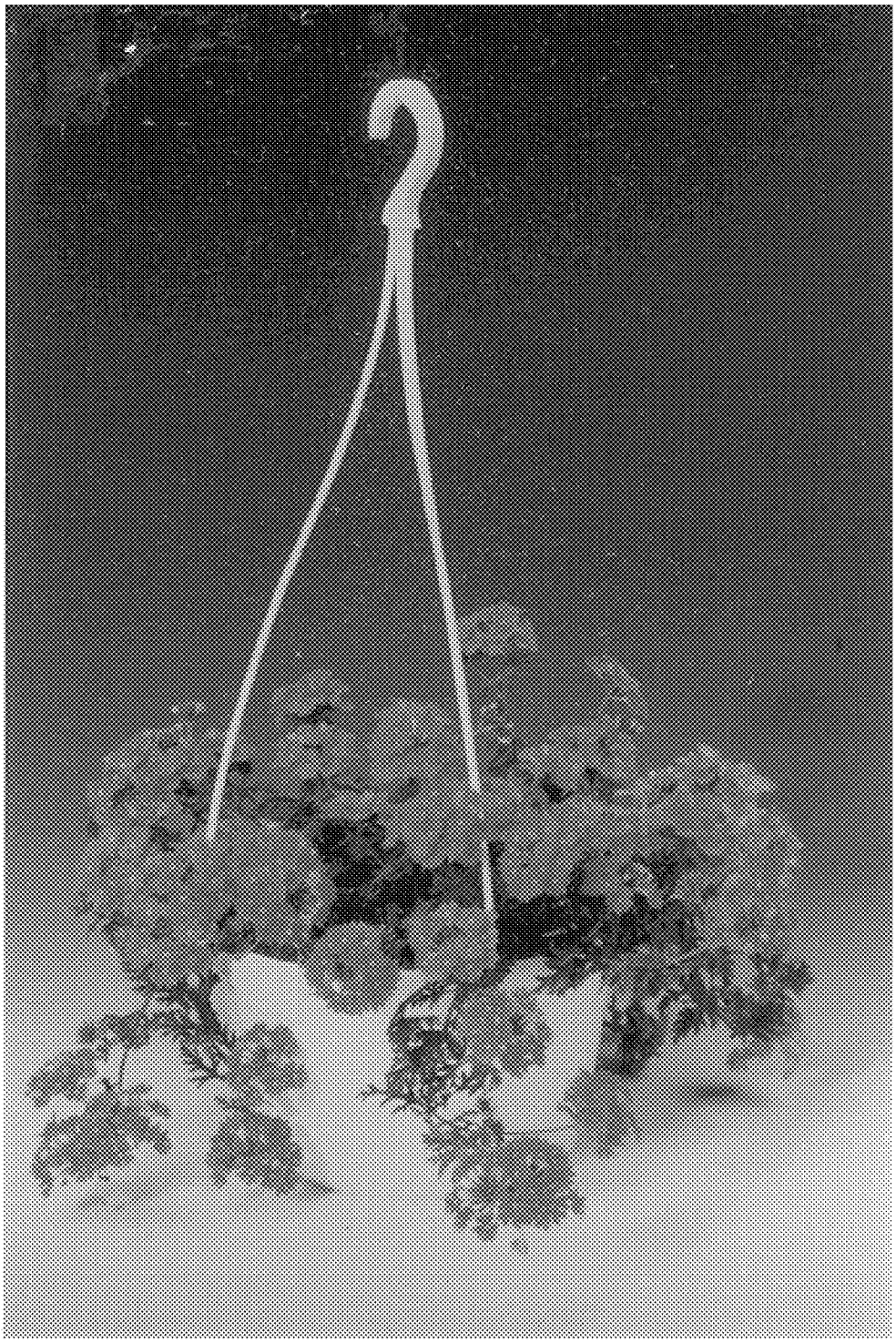
FIG. 1 depicts the spreading and hanging habit of the mature plant, while FIG. 2 provides a more detailed depiction of the blooms and foliage.
Figure 2:
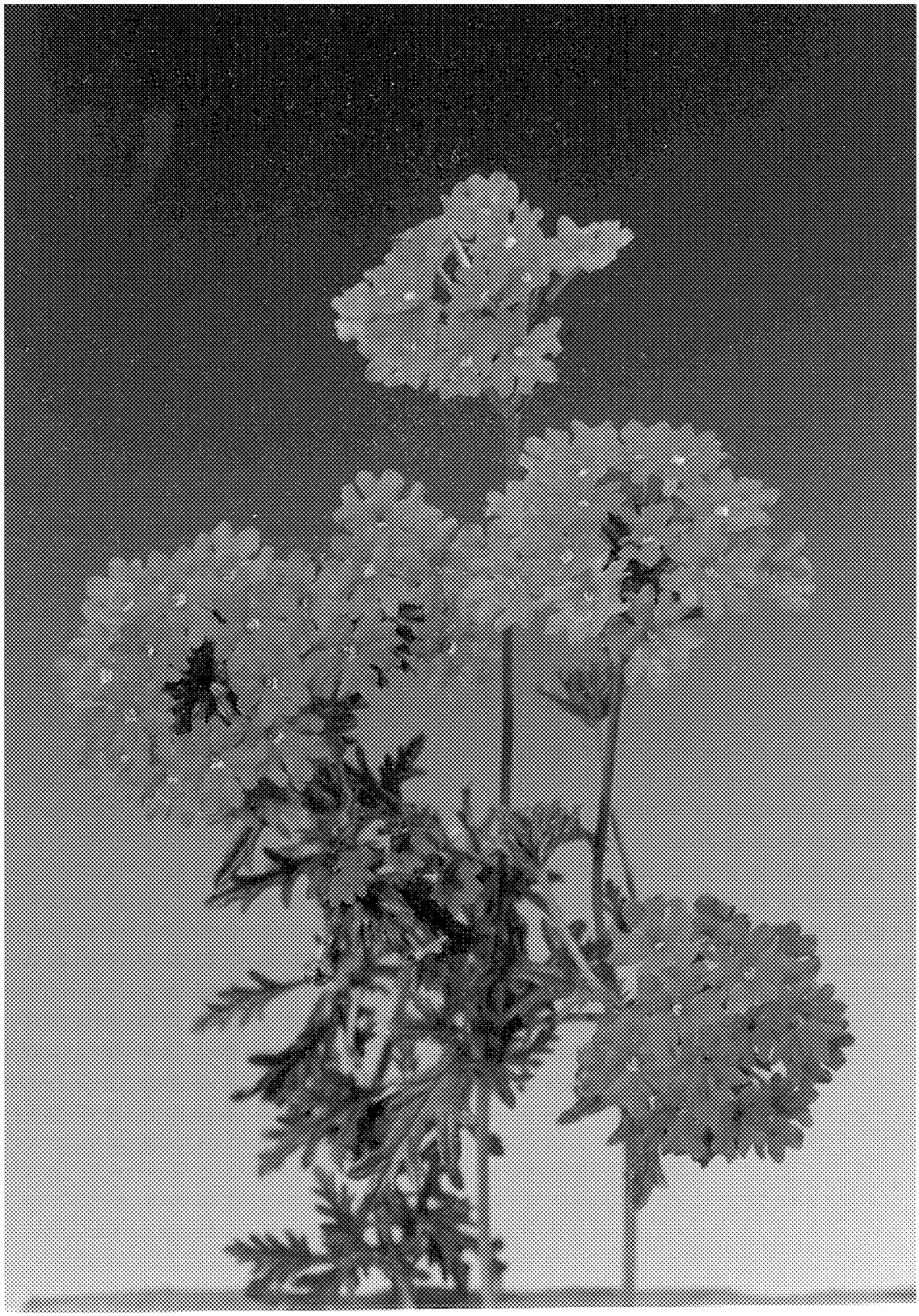

Classification:
*Botanical.*—*Verbena×hybrida.*
Parentage:
*Female parent.*—A seedling named W720 is one of our seedlings from our W-generation of plants bred in 1994.
*Pollen parent.*—A seedling named T593 is one of our seedlings from our T-generation of plants bred in 1991.
Growth habit: Semi-erect, later spreading.
Plant height: 20–30 cm.
Spreading area of plant: 50–70 cm.
Strength: Good.
Branching character: After pinching 7–9 breaks occur.
Blooming period: From April until November.

The Stem

Diameter: 1.5–2 mm.
Cross section: Tetragonal.
Anthocyan pigmentation: Absent.
Length of internode: 20–45 mm, depending on the light where the plant is grown.
Pubescence: Pubescence is present.

The Foliage

Phyllotaxis: Opposite.
Shape of blade: Cleft to parted.
Length: 25–40 mm.
Width: 20–32 mm.
Depth of incision: 10–20 mm.
Number of incisions per leaf: Many: more than 5.
Color:
*Upper side.*—Medium green 141B.
*Lower side.*—Light green 138A.
Pubescence: Some pubescence is present on both sides of the leaf.
Length of petiole: 10–15 mm.
Color of petiole: Medium green 141B.

The Bud

Peduncle length: 30–50 mm, depending on season.
Size:
*Diameter.*—2 mm.
*Length.*—8–12 mm.
Shape: Long.
Color: Medium green 141A.
Sepals:
*Color.*—Green 137D.
*Form.*—Upright.

The Flower

Direction: Ascending.
Diameter: 18–20 mm.
Height: 16–18 mm.
Borne: In a cluster.
Form: Flat and symmetrical.
Cluster: Corymb.
Color:
*Upper surface.*—Neon-rose 52A, later 52B.
*Lower surface.*—Pink 63B, later 63C.
Eye: A very small (2 mm) pink-white eye (159D) is present.
Margins: A small pink-white stripe (63C) on the lower petals.
Overlapping of petals: Separate.
Corymb:
*Length.*—20–40 mm.
*Diameter.*—40–50 mm.
Calyx: Length of 10–12 mm.
Anthocyan pigmentation of calyx limb: Absent.
No. of flowers per corymb: 20–30.
Flowers in bloom at one time 16–18.
Duration of flowering:
*Flower.*—3–5 days.
*Inflorescence.*—10–12 days.
Fragrance: A very soft rosy-sweet fragrance.
Reproductive organs: 1 pistil, 5 stamens. Seeds are formed in a very low frequency.
Physiological and ecological characteristics: Strong resistance to pests and diseases, particularly powdery mildew.

I claim:

1. A new and distinct variety of Verbena plant, substantially as herein illustrated and described, characterized particularly as to novelty by large neon-rose blooms, early flowering, and a growing habit that is first semi-erect but later spreading and hanging.

* * * * *